US00PP29817P2

(12) United States Plant Patent
Pierce

(10) Patent No.: US PP29,817 P2
(45) Date of Patent: Nov. 6, 2018

(54) ***CALIBRACHOA* PLANT NAMED 'CBRZ0013'**

(50) Latin Name: *Calibrachoa hybrida*
Varietal Denomination: CBRZ0013

(71) Applicant: SYNGENTA PARTICIPATIONS AG, Basel (CH)

(72) Inventor: Robert O. Pierce, Watsonville, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,920

(22) Filed: Aug. 23, 2017

(51) Int. Cl.
*A01H 5/02* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — Dale Skalla

(57) ABSTRACT

A new *Calibrachoa* plant named 'CBRZ0013' particularly distinguished by the mid-sized white flowers green foliage, good branching, early flowering, and a moderately compact plant habit, and has little sensitivity to soil pH.

1 Drawing Sheet

Latin name of the genus and species of the plant claimed: *Calibrachoa hybrida.*

Varietal denomination: 'CBRZ0013'.

BACKGROUND OF THE NEW PLANT

The present invention comprises a new *Calibrachoa*, botanically known as *Calibrachoa hybrida*, and hereinafter referred to by the variety name 'CBRZ0013'.

'CBRZ0013' is a product of a planned breeding program. The new cultivar has mid-sized white flower, green foliage, good branching, late flowering, and a moderately compact, semi-trailing plant habit, and has little sensitivity to soil pH.

'CBRZ0013' originated from a hybridization made in March 2010 in a greenhouse in Gilroy, Calif., USA. The female parent was the commercial plant variety 'Cali White CB298', 'G0078-2'. The male parent of 'CBRZ0013' was another white flowered plant known as '1140-6'.

The resulting seeds were sown in August 2010 and 'CBRZ0013' was selected as one flowering plant within the progeny of the stated cross in November 2010 in a controlled environment in Gilroy, Calif.

The first act of asexual reproduction of 'CBRZ0013' was accomplished when vegetative cuttings were propagated from the initial selection in the spring of 2011 in a controlled environment in Gilroy, Calif.

BRIEF SUMMARY OF INVENTION

Horticultural examination of plants grown from cuttings of the plant initiated in the late spring of 2011, and continuing thereafter, has demonstrated that the combination of characteristics as herein disclosed for 'CBRZ0013' are firmly fixed and are retained through successive generations of asexual reproduction.

'CBRZ0013' has not been observed under all possible environmental conditions. The phenotype may vary significantly with variations in environment such as temperature, light intensity, and day length.

A Plant Breeder's Right for this cultivar was applied for in the European Union on Aug. 10, 2017, No. 2017/1997. 'CBRZ0013' has not been made publicly available prior to the effective filing date of this application, notwithstanding any disclosure that may have been made less than one year prior to the effective filing date of this application by the inventor or another who obtained 'CBRZ0013' directly from the inventor.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'CBRZ0013' with colors being as true as possible with an illustration of this type.

Figure 1:
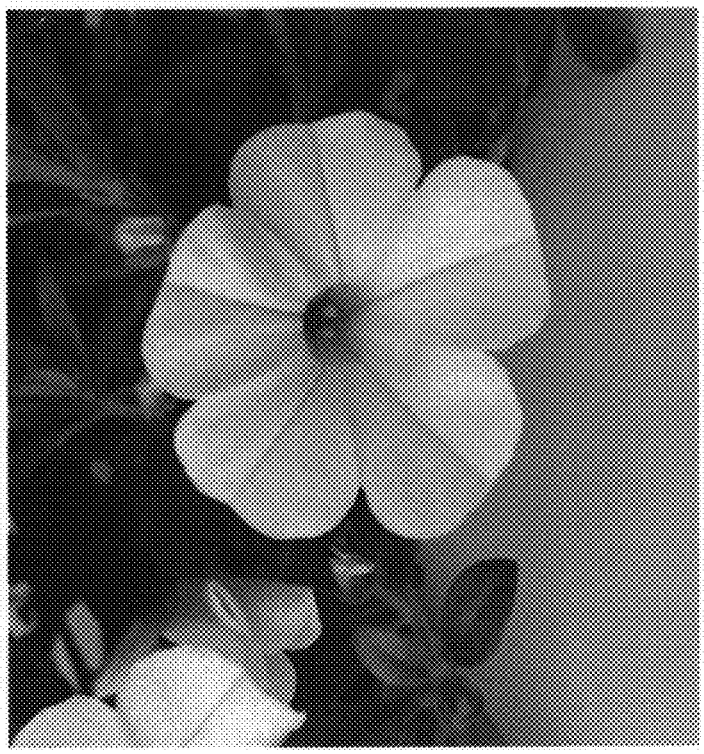
Figure 2:
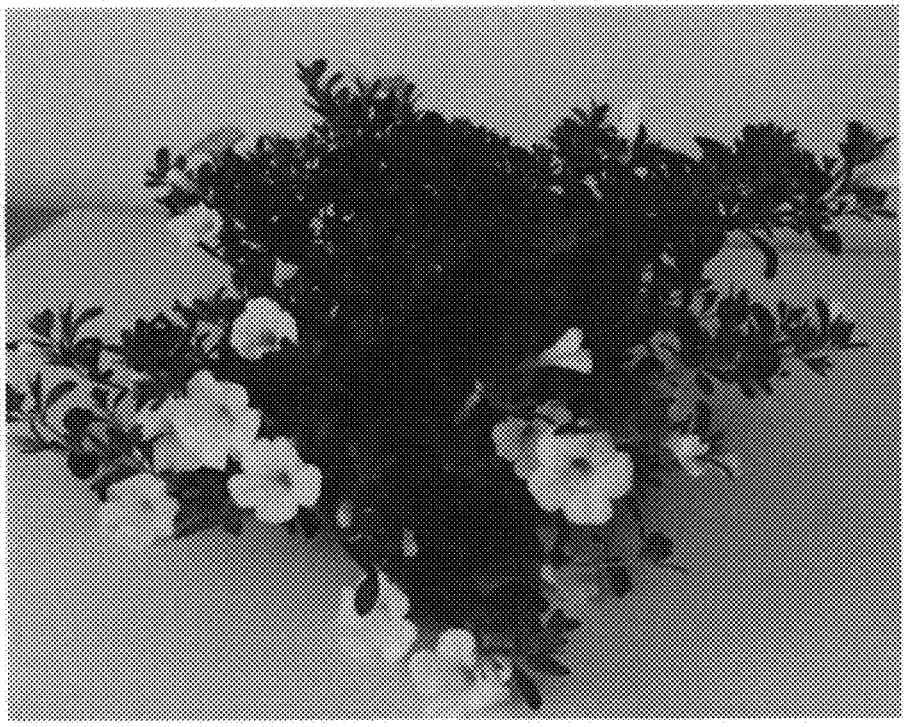

The photographic drawing shows in FIG. 1 a close-up of the flowers and in FIG. 2 a flowering plant of the new variety.

DETAILED BOTANICAL DESCRIPTION

The aforementioned photographs were taken in April 2017 in Gilroy, Calif.,

The measurements and observations were made in Gilroy, Calif. on plants grown in an indoor trial.

Color references are made to The Royal Horticultural Society Colour Chart (R.H.S.) 2001.

TABLE 1

DIFFERENCES BETWEEN THE NEW VARIETY 'CBRZ0013' AND A SIMILAR VARIETY

| | 'CBRZ0013' | 'CALLIE WHITE CB298' |
|---|---|---|
| Main flower color: | White | White |
| Earliness to flower: | Early under short photoperiod | Late under short photoperiod |

TABLE 1-continued

DIFFERENCES BETWEEN THE NEW VARIETY 'CBRZ0013' AND A SIMILAR VARIETY

| | 'CBRZ0013' | 'CALLIE WHITE CB298' |
|---|---|---|
| Plant habit as a young plant: | Compact and rounded with flowers across the top of the plant | More trailing plant |

Plant:

*Form, growth and habit*.—Semi-upright stems, compact and mounding, very well branched.

*Plant height*.—7-10 cm.

*Plant height* (*inflorescence included*).—About 7-10 cm.

*Plant width*.—40-45 cm.

*Quantity of main branches*.—18-23.

*Quantity of secondary branches*.—4-6 per basal branch.

*Time to produce a flowering plant*.—7-8 weeks for a 12 cm pot (from planting of rooted cuttings).

Roots:

*Number of days to initiate*.—18-21 days at about 22° C.

*Number of days to produce a rooted cutting*.—21-24 days at 22° C.

*Type*.—Fibrous.

*Color*.—RHS 158D.

Stem:

*Color of stem*.—Mainly RHS 138B.

*Length of stem*.—Approximately 15-20 cm.

*Diameter*.—0.15-0.2 cm.

*Length of internodes*.—1.7-2.0 cm.

*Texture*.—Hairs.

Foliage:

*Immature leaf, color of upper surface*.—RHS 137C.

*Immature leaf, color of lower surface*.—RHS 137C.

*Mature leaf, color of upper surface*.—RHS 137A.

*Mature leaf, color of lower surface*.—RHS 137C.

*Leaf blade, length*.—2.0-4.0 cm.

*Leaf, width*.—1.0-2.0 cm.

*Shape*.—Elliptical, narrow.

*Base shape*.—Attenuate.

*Apex shape*.—Obtuse.

*Margin*.—Entire.

*Texture*.—Hairs.

*Color of veins, upper surface*.—RHS 138B.

*Color of veins lower surface*.—RHS 138B.

*Petiole color*.—RHS 138B.

*Petiole length*.—0.1-0.3 cm.

*Diameter of petiole*.—0.1 cm.

*Texture*.—Hairs.

Inflorescence:

*Type*.—Flowers solitary in upper leaf axis and slanting upright or outwards.

*Quantity of inflorescences per plant*.—Approximately 35-40.

*Lastingness of individual flowers*.—About 7-9 days.

*Fragrance*.—None.

*Duration of flowering*.—Continuous flowering throughout the summer.

Pedicel:

*Color of pedicel*.—RHS 144A.

*Length of pedicel*.—1.5-2.0 cm.

*Diameter of pedicel*.—1.0 mm.

*Texture of pedicel*.—Hairs.

Flower:

*Immature flowers, corolla upper surface*.—Shiny closest to RHS 155D.

*Immature flowers, corolla lower surface*.—Closest to RHS 155D with RHS 145A vein.

*Mature flowers, color upper surface*.—Shiny closest to RHS 155D.

*Mature flowers, color lower surface*.—Closest to RHS 155D with RHS 145A vein.

*Flower horizontal diameter*.—3.3-3.7 cm.

*Flower height* (*vertical*).—2.5-3.0 cm.

*Corolla tube length*.—About 1.1 cm.

*Petal apex shape*.—Truncate.

*Margin*.—Entire.

*Waviness of petals*.—Weak to medium.

*Petal lobation*.—Moderate.

*Corolla texture*.—'Face' papillose and glabrous; rear side with short hair.

*Corolla tube color inside*.—RHS 1B with RHS 145A veins.

*Corolla tube color outside*.—RHS 1D with RHS 145A veins.

Bud (just before opening):

*Color at apex*.—RHS 155D with RHS 145A vein.

*Length*.—2.0-2.5 cm.

*Width* (*upper end*).—0.7-1.1 cm.

*Shape*.—Oblong.

Calyx:

*Number of sepals*.—5.

*Color of sepals, adaxial or upper surface*.—Closest to RHS 144A.

*Color of sepals, abaxial or lower surface*.—RHS 143A.

*Length of sepals*.—1.1-1.5 cm.

*Width of sepals*.—0.2-0.3 cm.

*Sepal shape*.—Lanceolate.

*Apex shape*.—Obtuse to acute.

*Margins*.—Entire.

*Texture*.—Hairs.

Reproductive organs:

*Pistil*.—1.

*Length*.—1.3 cm.

*Style color*.—RHS 145B.

*Style length*.—0.8-0.9 cm.

*Stigma color*.—RHS 144B.

*Number of stamens*.—5.

*Color of filaments*.—RHS 4D.

*Length filaments*.—0.7-1.1 cm.

*Color of pollen*.—RHS 13B.

*Pollen amount*.—Moderate.

*Fertility/seed set*.—Not observed on this hybrid.

*Disease/pest resistance*.—Not observed on this hybrid.

What is claimed is:

1. A new and distinct variety of *Calibrachoa* plant named 'CBRZ0013', substantially as illustrated and described herein.

* * * * *